US011479877B2

(12) United States Patent
Ladner et al.

(10) Patent No.: US 11,479,877 B2
(45) Date of Patent: Oct. 25, 2022

(54) DISPLAY LIBRARY PROCESS

(71) Applicant: Takeda Pharmaceutical Company Limited, Osaka (JP)

(72) Inventors: Robert Charles Ladner, Ijamsville, MD (US); Shannon Hogan, Arlington, MA (US); Kristin L. Rookey, Lebanon, NH (US)

(73) Assignee: Takeda Pharmaceutical Company Limited, Osaka (JP)

( * ) Notice: Subject to any disclaimer, the term of this patent is extended or adjusted under 35 U.S.C. 154(b) by 129 days.

(21) Appl. No.: 16/748,441

(22) Filed: Jan. 21, 2020

(65) Prior Publication Data

US 2020/0231962 A1 Jul. 23, 2020

Related U.S. Application Data

(62) Division of application No. 15/607,300, filed on May 26, 2017, now Pat. No. 10,577,598, which is a division of application No. 14/048,526, filed on Oct. 8, 2013, now Pat. No. 9,670,481, which is a division of application No. 10/656,350, filed on Sep. 5, 2003, now Pat. No. 8,557,743.

(60) Provisional application No. 60/408,624, filed on Sep. 5, 2002.

(51) Int. Cl.
| | | |
|---|---|---|
| *C40B 30/04* | (2006.01) | |
| *B03C 1/01* | (2006.01) | |
| *B03C 1/28* | (2006.01) | |
| *G01N 33/569* | (2006.01) | |
| *C12N 15/10* | (2006.01) | |

(52) U.S. Cl.
CPC .............. *C40B 30/04* (2013.01); *B03C 1/01* (2013.01); *B03C 1/288* (2013.01); *C12N 15/1037* (2013.01); *G01N 33/56983* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,336,173 A | 6/1982 | Ugelstad |
| 4,459,378 A | 7/1984 | Ugelstad |
| 5,183,740 A | 2/1993 | Ligler et al. |
| 5,223,409 A | 6/1993 | Ladner et al. |
| 5,403,484 A | 4/1995 | Ladner et al. |
| 5,432,018 A | 7/1995 | Dower et al. |
| 5,571,681 A | 11/1996 | Janda |
| 5,759,820 A | 6/1998 | Hornes et al. |
| 5,854,051 A | 12/1998 | Chandrashekar et al. |
| 5,969,108 A | 10/1999 | McCafferty et al. |
| 5,976,813 A | 11/1999 | Beutel et al. |
| 6,022,729 A | 2/2000 | Steinbuchel et al. |
| 6,326,155 B1 | 12/2001 | Maclennan et al. |
| 6,423,538 B1 | 7/2002 | Wittrup et al. |
| 6,562,622 B1 | 5/2003 | Coia et al. |
| 6,649,419 B1 | 11/2003 | Anderson |
| 6,797,480 B1 | 9/2004 | Srivastava |
| 8,557,743 B2 | 10/2013 | Ladner et al. |
| 9,670,481 B2 | 6/2017 | Ladner et al. |
| 10,577,598 B2 | 3/2020 | Ladner et al. |
| 2002/0058269 A1 | 5/2002 | Nock et al. |
| 2004/0180327 A1 | 9/2004 | Ladner et al. |
| 2004/0214242 A1 | 10/2004 | Goletz et al. |

FOREIGN PATENT DOCUMENTS

WO 2001/002554 A2 1/2001

OTHER PUBLICATIONS

Al-Bukhari et al., An immuno-precipitation assay for determining specific interactions between antibodies and phage selected from random peptide expression libraries. J Immunol Methods. Jun. 1, 2002;264(1-2):163-71.
Barbas et al., Phage Display: A Laboratory Manual. Cold Spring Harbor Laboratory Press. Cold Spring Harbor, NY; Chapter 10. 10.12-10.15, 2001.
Barbas et al., Phage Display: A Laboratory Manual. Cold Spring Harbor Laboratory Press. Cold Spring Harbor, NY; Chapter 17. 17.12-17.32, 2001.
Barbas et al., Phage Display: A Laboratory Manual. Cold Spring Harbor Laboratory Press. Cold Spring Harbor, NY; Chapter 19. 19.1-19.41, 2001.
Chames et al., Improving the Affinity and the Fine Specificity of an Anti-Cortisol Antibody by Parsimonious Mutagenesis and Phage Display. J Immunol. Nov. 15, 1998;161(10):5421-9.
Goletz et al., Selection of large diversities of antiidiotypic antibody fragments by phage display. J Mol Biol. Feb. 1, 2002;315(5):1087-97.
Harrison et al., Screening of phage antibody libraries. Methods Enzymol. 1996;267:83-109.
Hogan et al., URSA: ultra rapid selection of antibodies from an antibody phage display library. Biotechniques. Apr. 2005;38(4):536, 538.
Ivanenkov et al., Erratum in: Targeted delivery of multivalent phage display vectors into mammalian cells. Biochim Biophys Acta Sep. 21, 1999;1451(2-3):364.
Ivanenkov et al., Targeted delivery of multivalent phage display vectors into mammalian cells. Biochim Biophys Acta. Jan. 11, 1999;1448(3):463-72.
Kay et al., Phage Display of Peptides and Proteins: A Laboratory Manual. Academic Press, Inc. San Diego, CA; 1996. Chapter 6, p. 99-102.

(Continued)

*Primary Examiner* — Christian C Boesen
(74) *Attorney, Agent, or Firm* — Wolf, Greenfield & Sacks, P.C.

(57) ABSTRACT

Disclosed are methods for identifying desired members from a display libraries, including bacteriophage display libraries. Display library members can be amplified in the presence of a target compound so that cycles of selection can be rapidly completed.

5 Claims, No Drawings
Specification includes a Sequence Listing.

(56) References Cited

OTHER PUBLICATIONS

Kim et al., Viable deletions of the M13 complementary strand origin. Proc Natl Acad Sci USA. Nov. 1981;78(11):6784-8.

Konthur et al. Automation of Phage Display for High-Throughput Antibody Development. Targets. 2002;1(1):30-6.

Larocca et al., Evolving phage vectors for cell targeted gene delivery. Curr Pharm Biotechnol. Mar. 2002;3(1):45-57.

Larocca et al., Receptor-targeted gene delivery using multivalent phagemid particles. Mol Ther. Apr. 2001;3(4):476-84.

Lou et al., Antibodies in haystacks: how selection strategy influences the outcome of selection from molecular diversity libraries. J Immunol Methods. Jul. 1, 2001;253(1-2):233-42.

Markland et al., Iterative optimization of high-affinity proteases inhibitors using phage display. 1. Plasmin. Biochemistry. Jun. 18, 1996;35(24):8045-57.

O'Brien et al. (eds), Antibody Phage Display, Methods and Protocols. Humana Press. Totowa, NJ; 137-9; 147-57; 219-226; 2002.

Savingv et al., The cloning of human genes using cDNA phage display and small-molecule chemical probes. Comb Chem High Throughput Screen. Nov. 2001;4(7):593-7.

Sawyer et al., Methodology for selection of human antibodies to membrane proteins from a phage-display library. J Immunol Methods. May 26, 1997;204(2):193-203.

Sche et al., Display cloning: functional identification of natural product receptors using cDNA-phage display. Chem Biol. Oct. 1999;6(10):707-16. Erratum in: Chem Biol Apr. 2001;8(4):399-400.

Sche et al., Erratum in: Display cloning: functional identification of natural product receptors using cDNA-phage display. Chem Biol Apr. 2001;8(4):399-400.

Zhuang et al., A kinetic model for a biopanning process considering antigen desorption and effective antigen concentration on a solid phase. J Biosci Bioeng. 2001;91(5):474-81.

SEQUENCE LISTING

<160> NUMBER OF SEQ ID NOS: 12

<210> SEQ ID NO 1
<211> LENGTH: 4
<212> TYPE: PRT

```
<213> ORGANISM: Artificial Sequence
<220> FEATURE:
<223> OTHER INFORMATION: Synthetic

<400> SEQUENCE: 1

His Pro Gln Phe
1

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

His Asp Thr Gly Phe Ile Asn Asn Asn Gly Pro Thr His Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Pro Tyr Lys Gly Ser Val Glu Asn Gly Ala Tyr Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Asp Thr Lys Ser Asn Val Tyr Gly Lys Asn His Asp Thr Gly
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Ile Gly Asp Ala His Tyr Ile Gly Thr Arg Pro Asp
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Trp His Pro Gln Phe Ser Ser
1               5

<210> SEQ ID NO 7
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 7

His Asp Thr Gly Trp His Pro Gln Phe Ser Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

His Asp Thr Gly Phe His Pro Gln Phe Gly Pro Thr His Glu
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Pro Tyr Lys Gly Ser Trp His Pro Gln Phe Ser Ser Gly Ala Tyr Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Asp Thr Lys Ser Trp His Pro Gln Phe Ser Ser His Asp Thr Gly
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Ile Gly Asp Ala Trp His Pro Gln Phe Ser Thr Arg Pro Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gly Pro Cys His Pro Gln Phe Pro Arg Cys Tyr Ile
1               5                   10
```

DISPLAY LIBRARY PROCESS

CROSS-REFERENCE TO RELATED APPLICATIONS

This application is a divisional of U.S. application Ser. No. 15/607,300, filed May 26, 2017, which is a divisional of U.S. application Ser. No. 14/048,526, filed on Oct. 8, 2013, now U.S. Pat. No. 9,670,481, which is a divisional of U.S. application Ser. No. 10/656,350, filed on Sep. 5, 2003, now U.S. Pat. No. 8,557,743, which claims priority to U.S. Provisional Application Ser. No. 60/408,624, filed on Sep. 5, 2002, the contents of each of which are incorporated by reference herein in their entirety.

BACKGROUND

Display libraries are diverse collections of proteins in which each member links a particular protein of the library to the nucleic acid encoding it. Members of display libraries that have a particular property, frequently a binding affinity for a target compound of interest, can be selected from the library.

One common implementation of a display library is phage display. Phage display uses bacteriophage particles as vehicles for linking a diversified protein to the nucleic acid encoding it. The diversified nucleic acid is packaged within the bacteriophage, and generally the encoded protein on the phage surface. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *Proc Natl Acad Sci USA* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

One typical method of phage display includes: a) contacting a target compound with the library of proteins or peptides displayed on phage, b) separating the bound phage from the unbound phage (typically by washing unbound phage and eluting bound phage), c) infecting *E. coli* with the separated population of phage that bind, d) growing the infected cells to produce more phage, e) separating the amplified phage from the cells, and f) repeating steps (a)-(e) up to five times. Typically, each cycle of steps (a)-(e) takes one to five days and produces far more phage than are needed. Whereas about $10^{13}$ to $10^{15}$ phage are produced by overnight growth and purification, only ~$10^{11}$ to $10^{12}$ are used as input for the next round.

One known variation on the above selection method is a method that includes eluting phage that bind to a target compound, and recontacting the eluted phage to the target compound. Markland et al. (*Biochemistry* (1996) 35:8045-8057). The recontacting is effected without amplifying the eluted phage. After recontact, phage are eluted again from the target.

SUMMARY

The methods described here are applicable at least to libraries that are based on bacteriophage with a substantially complete genome (e.g., including a modified gene III) and to libraries that are based on bacteriophage particles that include a phagemid nucleic acid. The terms "bacteriophage library member" and "phage" encompass members of both types of libraries. The term "bacteriophage particle" refers to a particle formed of bacteriophage coat proteins that packages a nucleic acid. The packaged nucleic acid can be a modified bacteriophage genome or a phagemid, e.g., a nucleic acid that includes a bacteriophage origin of replication but lacks essential phage genes and cannot propagate in *E. coli* without help from "helper phage" or phage genes supplied in trans.

In one aspect, the invention features a method that includes:

a) forming a mixture comprising a plurality of diverse display phage, a target, and a support, wherein each phage of the plurality displays a heterologous protein component on its surface and each phage includes a nucleic acid encoding the heterologous protein component, the heterologous protein component being a member of a set of diverse protein components;

b) forming phage-immobilized target complexes, each of which comprises a phage from the plurality which binds the target and the target immobilized to the support;

c) separating phage that do not bind to the target from the phage-immobilized target complexes;

d) contacting host cells with the phage-immobilized target complexes (or phage-target complexes derived from phage-immobilized target complexes) so that the host cells are infected by phage from the phage-immobilized target complexes to yield a first population of infected cells; and e) producing replicate phage from the infected cells in the presence of the target thereby forming replicate phage-immobilized target complexes.

In one embodiment, the method further includes: f) separating replicate phage that do not bind to the target from the replicate phage-immobilized target complexes. The method can still further include: g) contacting host cells with the replicate phage-immobilized target complexes (or replicate phage-target complexes derived from replicate phage-immobilized target complexes) so that host cells are infected with the replicate phage to yield a second population of infected cells. The method can be used to select phage that encode a target binding protein from a plurality of display phage.

In a related aspect, the invention features a method that includes:

a) forming a mixture comprising a plurality of diverse display phage, a first target, and a support, wherein each phage of the plurality has a heterologous protein component physically attached to its surface and each phage includes a nucleic acid encoding the heterologous protein component, the heterologous protein component being a member of a set of diverse protein components;

b) forming phage-immobilized target complexes, each of which comprises a phage from the plurality which binds the first target and the first target immobilized to the support;

c) separating phage that do not bind to the first target from the phage-immobilized target complexes;

d) contacting host cells with the phage-immobilized target complexes (or phage-target complexes derived from phage-immobilized target complexes) in a suitable growth medium so that the host cells are infected by phage from the phage-immobilized target complexes to yield a first population of infected cells;

e) producing replicate phage from the infected cells in the presence of a second target thereby forming replicate phage-immobilized target complexes that include replicate phage that bind to the second target and the second target immobilized to a support;

f) separating replicate phage that do not bind to the second target from the replicate phage-immobilized target complexes; and g) contacting host cells with the replicate phage-immobilized target complexes (or replicate phage-target complexes derived from replicate phage-immobilized target complexes) so that host cells are infected with the replicate phage to yield a second population of infected cells. The first and second target can be the same or different.

For these methods and other methods described herein, it is understood that the mixture can include other components, for example, helper phage, and phage which package the nucleic acid, but do not include the encoded protein component (as may arise from use of a phagemid system). Such phage may be present in addition to the plurality of diverse display phage.

In one embodiment, the methods further include recovering the second population of infected cells or phage produced by the second population of infected cells.

In one embodiment, the methods further include repeating steps e) to g) at least once. In one embodiment, steps a) to g) are conducted in the same vessel. In another embodiment, steps d) to e) occur in the same vessel. In still another embodiment, steps d) to e) occur in different vessels. In one embodiment, steps b) to g) are conducted without addition of the target, e.g., the target used is present from step a). In another embodiment, step e) includes supplying the mixture in which the replicate phage are produced with an additional amount of the target. In one embodiment, the target is immobilized prior to forming the mixture. In another embodiment, the target is not immobilized prior to forming the mixture.

In one embodiment, the methods further include one or more of: during step e), fewer than 5000, 4000, 2000, 1000, 700, 500, 300, or 100 progeny phage are produced for each phage that infects one of the host cells; step e) is completed in less than 4, 3, 2 1.5, 1, or 0.5 hours; during step e), the host cells divide less than seven, six, five, four or three times; and during step e), an antibiotic whose resistance is encoded by a nucleic acid within each phage is present or absent. Time between the contacting d) and the separating f) can be less than 240, 120, 90, 80, 60, 45, 40, or 30 minutes and may be at least 30, 45, 60, 80, or 90 minutes.

The target can be immobilized to the support prior to step a).

In one embodiment, the target is a cell. In one embodiment, the target is a macromolecule, e.g., a macromolecule having a molecular weight of between 500 Da and 600 KDa, e.g., between 7 and 150 KDa. (e.g., an isolated or partially purified macromolecule). For example, the target is a protein. The protein can include one or more post-translational modifications, e.g., glycosylation.

The host cells are typically bacterial cells, e.g., E. coli cells, e.g., $F^+$ E. coli. In a cycle of one embodiment, during step e) and/or g), the host cells are cells of a mutator strain.

In one embodiment, the producing includes a change in temperature, e.g., of at least 5, 7, or 10° C. In one embodiment, the producing e) includes contacting the host cells with an agent that alters a property of the host cells. For example, the agent comprises a compound that alters regulation of transcription (e.g., IPTG).

Each phage of the plurality can include a gene that provides resistance to an antibiotic and the producing e) can occurs in the absence or presence of the antibiotic. For example, for very short burst times, the antibiotic may be omitted.

In one embodiment, each phage of the plurality includes genes sufficient for phage replication in a host cell. In another embodiment, each phage of the plurality is a phagemid. The producing e) can include contacting helper phage to the host cells.

The methods can further include characterizing the nucleic acid encoding the respective heterologous protein component from one or more phage produced by cells of the second population and/or characterizing the binding interaction between the target and the heterologous protein component of one or more phage produced by cells of the second population. In one embodiment, the characterizing includes individually characterizing. The methods can further include evaluating infected host cells from the first or second population; or evaluating infected host cells from at least one repeat (e.g., titering the infected host cells), e.g., each repeat.

A competing ligand can be present during an interval of the producing e). For example, the competing ligand binds to the target, e.g., to a specific epitope on the target. In another example, the competing ligand may be soluble and structurally homologous to at least a segment of the target. In this case, the competing ligand is not immobilized.

The diverse set of protein components can consist of between $10^3$ and $10^{12}$ different protein components, e.g., between $10^3$, $10^4$, $10^5$, $10^6$, $10^8$, or $10^9$, and $10^6$, $10^8$, $10^9$, $10^{10}$, $10^{11}$, or $10^{12}$. For example, the diverse set of protein components can be a set that are all derived from a particular protein scaffold or that are all designed to conform to a particular protein scaffold. For example, each protein component of the set can include one or more invariant positions that are identical among all the components of the set. In one embodiment, at least some of the invariant positions are cysteines, e.g., cysteines that form a disulfide bond. Exemplary protein scaffolds include an immunoglobulin variable domain, a cysteine loop (e.g., with a loop length of less than 15, 12, 9, or 6 amino-acid residues between the cysteine residues), a protease inhibitor, a conotoxin, and so forth.

In one embodiment, the method includes releasing the target from the solid support, e.g., by breaking a covalent or non-covalent attachment, e.g., reducing a disulfide bond and so forth. The releasing can provide a phage-target complex that can be contacted to host cells. In an embodiment, the solid support can be blocked, e.g., it can be blocked to different extents for at least some of the repeats.

The method can include other features described herein.

In another aspect, the invention features a method that includes: (a) providing a bacteriophage library that includes a plurality of bacteriophage members; (b) selecting a subset of the bacteriophage members; (c) infecting host cells with the members of the subset; (d) amplifying members of the subset; and (e) selecting a subset of the amplified members, thereby selecting members having desired binding from the bacteriophage library. During the amplifying of step d), fewer than 5000, 4000, 2000, 1000, 700, 500, or 300 progeny phage are produced for each phage that infects one of the host cells; the amplifying is completed in less than 4, 3, 2 1.5, 1, or 0.5 hours; during the amplifying, the host cells divide less than seven, six, five, four or three times; and during the amplifying, an antibiotic whose resistance is encoded by a nucleic acid within each phage is present or absent. The method can be used to select desired proteins or peptides from a bacteriophage library.

In one embodiment, the amplifying (d) occurs in the presence of a target, and step (e) includes selecting amplified members that bind to the target. For example, the target is a compound or cell that is immobilized during the amplifying (d).

In one embodiment, step (b) includes contacting the bacteriophage library to a target and a solid support, immobilizing members of the library that bind to the target, and separating members of the library that bind to the target from members of the library that do not bind to the target.

The method can include other features described herein.

In another aspect, the invention features a method that includes: a) providing a library of phage that each have a heterologous protein component, physically attached to the phage, and accessible wherein each protein component is a member of diverse set of different proteins; b) contacting phage of the library to a target; c) performing one or more cycles of:
  i) forming phage-immobilized target complexes, each of which includes (1) a phage that binds to the target by its heterologous protein component and (2) the target immobilized to a support,
  ii) separating phage that do not bind to the target from the phage-immobilized target complexes,
  iii) contacting phage from the phage-immobilized target complexes with host cells so that the host cells are infected by the phage from the phage-immobilized target complexes, and
  iv) producing phage from the infected cells in the presence of the target, the produced phage being replicates of phage that bind to the target; and
  d) recovering the nucleic acid encoding the heterologous protein component of one or more produced phage that bind to the target, thereby selecting a nucleic acid that encodes a binding protein for the target. The method can be used to select a nucleic acid that encodes a binding protein from a library of display phage.

In one embodiment, conditions of the separating in step ii) vary in stringency during the cycles. In one embodiment, at least two, three, four, or five cycles are performed. For example, each cycle is completed in less than 8, 7, 6, 5, 3, or 2 hours.

In one embodiment, the cycles are conducted in the same vessel. In another embodiment, the cycles occur in the same vessel. In still another embodiment, the cycles occur in different vessels. In one embodiment the cycles are conducted without addition of the target, e.g., the target used is present from step a). In another embodiment, step e) includes supplying the mixture in which the replicate phage are produced with an additional amount of the target.

In one embodiment, the methods further include one or more of: during step iv), fewer than 5000, 4000, 2000, 1000, 700, 500, 300, or 100 progeny phage are produced for each phage that infects one of the host cells; step iv) is completed in less than 4, 3, 2 1.5, 1, or 0.5 hours; during step iv), the host cells divide less than seven, six, five, four or three times; and during step iv), an antibiotic whose resistance is encoded by a nucleic acid within each phage is present or absent. Time between the contacting (iii) and the separating (ii) of the subsequent cycle can be less than 240-80, 120, 90, 60, 45, 40, or 30 minutes.

The target can be immobilized to the support prior to step i).

In one embodiment, the target is a cell. In one embodiment, the target is a macromolecule having a molecular weight of between 1 and 300 KDa (e.g., an isolated or partially purified macromolecule). For example, the target is a protein. The protein can include one or more post-translational modifications, e.g., glycosylation or phosphorylation.

The host cells are typically bacterial cells, e.g., *E. coli* cells, e.g., F+ *E. coli*. In a cycle of one embodiment, during step e) and/or g), the host cells are cells of a mutator strain.

In one embodiment, the producing includes a change in temperature, e.g., of at least 5, 7, or 10° C. In one embodiment, the producing e) includes contacting the host cells with an agent that alters a property of the host cells. For example, the agent comprises a compound that alters regulation of transcription (e.g., IPTG).

Each phage of the plurality can include a gene that provides resistance to an antibiotic, and the producing iv) can occur in the absence or presence of the antibiotic. For example, for very short burst times, the antibiotic may be omitted.

In one embodiment, each phage of the plurality includes genes sufficient for phage replication in a host cell. In another embodiment, each phage of the plurality is a phagemid. The producing iv) can include contacting helper phage to the host cells.

The methods can further include characterizing the nucleic acid encoding the respective heterologous protein component from one or more phage produced by cells of the second population and/or characterizing the binding interaction between the target and the heterologous protein component of one or more phage produced by cells of the second population. In one embodiment, the characterizing includes individually characterizing. The methods can further include evaluating infected host cells from the first or second population; or evaluating infected host cells from at least one repeat (e.g., titering the infected host cells).

A competing ligand can be present during an interval of the producing iv). For example, the competing ligand binds to the target, e.g., to a specific epitope on the target. In another example, the competing ligand may be soluble and structurally homologous to at least a segment of the target. In this case, the competing ligand is not immobilized.

The diverse set of protein components can consist of between $10^3$ and $10^{12}$ different protein components, e.g., between $10^3$, $10^4$, $10^5$, $10^6$, $10^8$, or $10^9$, and $10^6$, $10^8$, $10^9$, $10^{10}$, $10^{11}$, or $10^{12}$. For example, the diverse set of protein components can be a set that are all derived from a particular protein scaffold or that are all designed to conform to a particular protein scaffold. For example, each protein component of the set can include one or more invariant positions that are identical among all the components of the set. In one embodiment, at least some of the invariant positions are cysteines, e.g., cysteines that form a disulfide bond. Exemplary protein scaffolds include an immunoglobulin variable domain, a cysteine loop (e.g., with a loop length of less than 15, 12, 9, or 6 amino-acid residues between the cysteine residues), a protease inhibitor, a conotoxin, and so forth.

In one aspect, the invention features a method that includes: maintaining a plurality of host cells in the presence of a target compound, each host cell containing a nucleic acid encoding a candidate protein that is attachable a bacteriophage particle and that varies among the plurality of host cells, the maintaining being under conditions wherein the host cells of the plurality produce bacteriophage particles that include the attached candidate proteins; and immobilizing a subset of the bacteriophage particles, wherein the particles of the subset include attached candidate proteins that bind to the target compound. The method can further include, prior to the maintaining, contacting host cells to an insoluble support that has immobilized thereon a plurality of input bacteriophage particles, each encoding a different candidate protein, under conditions that enable the particles to infect the cells with nucleic acid encoding the respective candidate proteins. The method can also further include separating the immobilized subset from the host cells.

In one embodiment, the method further includes contacting the immobilized subset of particles with a given ligand that binds to a discrete epitope on the target compound and dissociating a particle of the immobilized subset; and, optionally, amplifying and/or recovering the dissociated particle.

Each of the bacteriophage particles produced by the cells can include a bacteriophage genome or a phagemid. For example, the bacteriophage particles are filamentous bacteriophage particles, such as derivatives of M13, f1, or fd.

In one embodiment, the target compound is a protein, and a non-target compound, at least 70% identical to the target compound is present during the maintaining. In one embodiment, the target compound is immobilized on an insoluble support prior to the maintaining. In another embodiment, the target compound is free in solution during an interval of the maintaining. The immobilizing can include attaching the target compound to an insoluble support, and/or washing the insoluble support. In some cases, the method can further include transferring the insoluble support from a first vessel to a second vessel.

The method can include other features described herein.

In another aspect, the invention features a method of amplifying a plurality of display library members. The method includes: amplifying a plurality of display library members in the presence of a target (e.g., a target compound) to yield a population of amplified display library members (e.g., bacteriophage display library members). In one embodiment, during or after the amplifying, at least a subset of the amplified display library members physically interact with the target compound. In one embodiment, at least a subset of the amplified display library members bind to the target compound. The method can further include a subset of the amplified display library members that bind to the target compound. The method can include other features described herein.

In still another aspect, the invention features a method of identifying members having a desired binding property from a bacteriophage library. The method includes: providing a bacteriophage library that includes a plurality of bacteriophage members; selecting a subset of the bacteriophage members; infecting host cells with the members of the subset; and amplifying members of the subset under at least one of the following conditions: (1) fewer than 5000, 500, or 100 progeny phage are produced for each input phage; (2) less than 4, 3, 2, 1, or 0.5 hours elapses; (3) the host cells divide less than 6 times; and (4) an antibiotic whose resistance is encoded by a nucleic acid within each bacteriophage member is not present; and selecting a subset of the amplified members. The method can include other features described herein.

In another aspect, the invention features a method of selecting members having a desired binding property from a bacteriophage library. The method includes: providing a first plurality of diverse bacteriophage, wherein the first plurality is characterized by a first titre; selecting a subset of the first plurality, wherein the subset is less than 0.01% of the first plurality; amplifying members of the subset to provide amplified members; and contacting a second plurality of bacteriophage to a target compound, wherein the second plurality if characterized by a second titre that is less than one-tenth of the first titre. In one embodiment, with respect to sequential cycles of binding and selection, the binding phage are propagated in situ and do not maintain the input level of phage. The advantage is that very much time is saved. The method can include other features described herein.

In still another aspect, the invention features a method of amplifying a display phage. The method includes: immobilizing phage that display a protein entity on their surface on a support that includes a target compound; contacting a host cell to the support under conditions that allow the immobilized phage to infect the host cell; and culturing the host cell in the presence of the support under conditions that enable production of replicates of the immobilized phage, thereby amplifying the immobilized phage. The method can include other features described herein.

In another aspect, the invention features a method of selecting a display library member. The method includes: amplifying a display library member in a defined nutritive medium that supports growth of a microorganism; and binding the amplified display library member to a target compound in the defined nutritive medium, e.g., a liquid medium. Typically the medium is buffered. The amplifying and the binding can be concurrent so that while some display library members are being produced, others, produced momentarily before can bind to the target compound if they have affinity and, optionally, specificity for it. The method can include other features described herein.

The invention also includes a library of display phage that includes a plurality of diverse display phage derived from a plurality of input display phage, the library consisting of fewer than 10,000 replicates of each input display phage, and that is isolated by a method including providing a plurality of input display phage that each interact with a target compound, and amplifying each of the input display phage under at least one of the following conditions (1) fewer than 5000, 1000, 500, or 200 progeny phage are produced for each input phage; (2) less than 4, 3, 2, 1, 0.8 hours elapses; and (3) an antibiotic whose resistance is encoded by a nucleic acid within each bacteriophage member is absent or present. The method can include other features described herein. For example, each phage can include a minor coat protein (e.g., gene IIIp) to which a candidate protein is attached (e.g., by a peptide bond). The candidate protein can include a immunoglobulin domain or an intramolecular disulfide bond. In addition, the invention features a binding reaction mixture that includes bacterial cells, each including a nucleic acid encoding a candidate protein that can be attached to a bacteriophage coat protein and able to produce a bacteriophage particle that includes the candidate protein attached thereto; and a target compound that can be immobilized on an insoluble support or that is immobilized to a insoluble support. In particular, the reaction mixture may include cells that are actively generating bacteriophage particles as opposed to lysogens or cells only recently infected. Thus, the reaction mixture can include bacteriophage particles produced by the bacterial cells. In one embodiment, the reaction mixture further includes the insoluble support. Typically the reaction mixture is aqueous, and may contain a buffering agent and/or a nutritive medium.

In another aspect, the invention features a method of processing a plurality of display phage. The method includes: (1) contacting a plurality of diverse display phage to a target compound; (2) separating phage that bind to the target compound from unbound phage; and (3) one or more cycles that include:
  a. infecting host cells with the phage that bind to the target compound in a first vessel;
  b. transferring the host cells to a second vessel,
  c. producing replicate phage from the infected cells in the presence of the target compound in the second vessel;
  d. separating phage that bind the target compound from the unbound phage and infected hosts cells;
  e. repeating a. to d. one or more times, e.g., one to six times;

In one embodiment, during at least one of the cycles the host cell is a mutator strain. The infecting can include contacting the host cells to the immobilized target compound bound to a display phage. The transferring can include binding infected cells to an insoluble support and disposing the insoluble support in the second vessel. In one embodiment, the insoluble support is a magnetically responsive particle.

In one embodiment, the cells include an exogenous chemical tag (e.g., biotin or an artificial peptide such as one present by an outer membrane protein) and the insoluble support includes a ligand that binds to the tag.

The method can include other features described herein.

In another aspect, the invention features a method of selecting a binding protein, the method including: providing complexes including a target compound and bacteriophage particles that each display a heterologous protein; contacting the complexes with a given ligand that binds to a discrete epitope of the target compound under conditions that cause dissociation of one or more of the bacteriophage particles; infecting host cells with the one or more dissociated bacteriophage particles; and maintaining the host cells in the presence of the target compound under conditions whereby replicates of the one or more dissociated bacteriophage particles are produced.

For example, the host cells can be maintained in a medium that is substantially free of the given ligand. The method can further include separating the host cells after the infecting from medium containing the given ligand.

The method can include other features described herein.

In another aspect, the invention features a method of selecting a subset of bacteriophage particles. The method includes: maintaining bacterial host cells in the presence of a target-presenting cell that includes a target compound accessible to medium surrounding the cell, the host cells containing nucleic acid encoding a plurality of different candidate proteins that are attachable a bacteriophage particle, the maintaining being under conditions wherein the bacterial host cells produce bacteriophage particles that include the attached candidate proteins; and separating a subset of the bacteriophage particles that bind to the target-presenting cells from the bacteriophage particles produced by the bacterial host cells.

For example, the separating the subset includes sedimenting the target-presenting cells and bacteriophage particles that bind to the target-presenting cells under conditions wherein less than 20, 10, or 5% of the bacterial host cells are sedimented. Separating the subset can include selectively attaching the target-presenting cells to an insoluble support using a ligand that recognizes the target-presenting cells but does not bind to the target compound. The method can include other features described herein.

In certain implementations, a method described herein is performed in a vessel, e.g., a vessel other than a flow chamber, e.g., a vessel with a single port or opening. In certain implementations, a method described herein is performed without using magnetic beads.

The term "polypeptide" refers to a polymer of three or more amino acids linked by a peptide bond. The polypeptide may include one or more unnatural amino acids. Typically, the polypeptide includes only natural amino acids. The term "peptide" refers to a polypeptide that is between three and thirty-two amino acids in length. A "protein" can include one or more polypeptide chains. Accordingly, the term "protein" encompasses polypeptides and peptides. A protein or polypeptide can also include one or more modifications, e.g., a glycosylation, amidation, phosphorylation, and so forth.

One of the advantages of some implementations described here is a greatly reduced time for performing multiple cycles of binding selection. Unlike some methods, the number of input phage in each successive cycle is reduced. For example, subsequent cycles can use a number of input phage that is at least one, two, or three orders of magnitude less than the initial cycle or the previous cycle. The amplification of binding phage in the presence of the target compound is one method for saving time.

The following describes the enrichment of binding phage using a phage production method of limited duration, e.g., a burst of phage. It is estimated that each infected *E. coli* cell produces a burst of approximately 1000 phage per cell; thereafter the cells produce 100 to 200 phage per cell per generation. Supposing that an initial library aliquot contains ~500 copies of each phage member, and that for each species that binds target, 5 to 50 phage/mid are captured, in the first burst, 5,000 to 50,000 copies of each binding species are released. After two rounds, there would be 50,000 to $5 \cdot 10^6$, assuming that 1% to 10% of the first burst is captured. Accordingly, growing the infected cells after two to four rounds provides a population of colonies having an increased percentage of peptides or proteins that bind the target.

The rapid selection methods enable at least three or four rounds of selection in a single day. The method can also be implemented using automation, e.g., a magnetic particle processor, liquid handling units, and the like. In some cases, members identified by the selection can be isolated, grown overnight, and analyzed so that results of the selection are available the following morning.

Some implementations also reduce the number of containers and surfaces for selection. For example, the same vessel can be used for all selections.

All patents, patent applications, and other references given herein are hereby incorporated by reference in their entirety for all purposes. U.S. Ser. No. 10/313,822, filed Dec. 6, 2002, is herein incorporated by reference in their entirety for all purposes.

DETAILED DESCRIPTION

In one aspect, the invention provides a variety of accelerated methods for identifying members having a desired binding property from display libraries, e.g., phage display libraries. Phage display libraries are used to provide a physical association between a protein to be displayed and the nucleic acid that encodes it. This nucleic acid, or "display gene", can include a secretion signal sequence, a segment that encodes the protein to be displayed and a segment that encodes an attachment moiety (of one or more amino acid residues) that causes the encoded protein to become attached to the phage particle. The segments that encode the attachment moiety are typically constant within the library. In one embodiment, the attachment moiety is an anchor domain, such as a phage coat protein or a fragment thereof. Other methods of attachment are also available, see, e.g., Crameri et al. (1994) Eur J Biochem 226(1):53-8 and WO 01/05950.

The protein to be displayed segment may be picked at will. For example, one can display linear or cyclic peptides, Kunitz domains, Kazal domains, Fabs (antibodies), conotoxins, and the like. It is possible to build phage libraries in which a very high fraction of phage particles contain a display gene according to the design of the library. In some libraries, a large fraction of the phage particles actually display the protein encoded by the insert of that phage. In phagemid libraries, it is often found that only a small fraction, e.g. 10%, of phage particles actually display the encoded library member. Nevertheless, many useful binding molecules have been selected from such libraries because the selection acts on a population that is 100 to 1000 times larger than the diversity of the library. Thus, each protein member that is genotypically represented is actually present on 10 to 100 phage particles (10% of 100 to 1000).

In one embodiment, the method includes amplifying a display library member in the presence of a target compound. The method can be used to identify members of the library that interact with the target compound. In another embodiment, the method restricts amplification to a limited interval or a burst so that the selection process rapidly advances, e.g., through successive cycles. Still other features are disclosed that enable improved selection of the display library. As noted above, the methods are applicable at least to bacteriophage and to phagemids, as well as other types of display libraries.

One exemplary method includes the following:
a. Contacting a plurality of diverse display phage to a target compound;
b. Separating phage that bind to the target compound from unbound phage;
c. Infecting host cells with the bound phage;
d. Producing replicate phage from the infected cells in the presence of the target compound ("phage production");
e. Separating phage that bind the target compound from the unbound phage and infected cells;
f. Repeating c. to e. one or more times, e.g., one to six times;
g. Recovering the bound phage, e.g., for individual characterization.

In the above example, each round of replicate phage production is carried out in the presence of target compound. The host cells are typically $F^+$ E. coli. The E. coli are maintained in the presence of the target compound during infection and during phage production by the infected cells. The cells can be maintained, e.g., for less than three division cycles, e.g., less than an hour. As soon as replicate phage emerge from the infected cells, they can bind to the target compound since the target compound is present during phage production. Moreover, it is not essential to purify or harvest the emerging phage during each cycle.

The time interval for step (d) can be, for example, between 30 to 120 minutes or between 45 to 60 minutes. Experimental observations of filamentous phage have demonstrated that most phage are internalized within 15 minutes of contact between phage and E. coli. Progeny start to appear about 30 minutes after contact in a burst of about 1000 phage per cell. Progeny production drops significantly after the first 45-60 minutes, although phage may still be produced at about 100-200 per cell per generation if cells are well nourished and aerated.

During the interval for phage production, the method can include a change in temperature. In an example of a phage library that displays immunoglobulins (e.g., Fab's or scFv's), the first 20 minutes can be carried out at 37° C. and a subsequent 25 minutes at 30° C. The lower temperature can improve the folding of some protein domains, e.g., an immunoglobulin domain. Also during this interval, an agent that alters a property of the host cell can be added. For example, in cases wherein production of the displayed protein is under control of an inducible promoter, then an inducer of that promoter can be introduced at an appropriate time during the incubation. In an example in which production of the displayed protein is controlled by a lacI regulated promoter, e.g., the lacZ promoter, a lac inducer, e.g., IPTG, can be added, e.g., at the tenth minute of the propagation step.

For many rapid cycling methods, it is not necessary to add antibiotic during phage production. However, in some implementations, particularly those in which phage production is greater than 60 minutes (e.g., between 60 and 120 minutes), an antibiotic can be added, e.g., after the initial 10 or 15 minutes during which infection occurs. The antibiotic is used to select for cells that are infected by phage that include a nucleic acid encoding resistance to the antibiotic.

The infected cells that are removed at step (e) after phage production can be reserved, e.g., for further analysis. For example, such cells can be titred, e.g., to determine the number of bound phage particles. In another example, individual cells are grown for ~16 hours at 30° C. to produce enough additional phage for analysis by ELISA, e.g., to get a measure of the affinity of display library members for the target compound. In still another example, the cells are plated and the individual display library nucleic acids are recovered from the cells and sequenced. Isolate picking, growing, ELISA assays, sequencing and other operations can be carried out by robots (see, e.g., "Automation," below). These methods provide a snap-shot of the selection process.

In a final cycle, phage infect host cells. The infected cells are grown, e.g., in liquid culture, on plates or combination thereof, e.g., at a density that results in individual colonies. The display phage vector generally includes an antibiotic-resistance gene such as bla which confers resistance to ampicillin. The corresponding antibiotic (e.g., ampicillin) is included in the growth medium so that only infected cells are grown and the display vector is retained. Since antibiotic resistance does not appear immediately, the antibiotic can be added after a delay, e.g., about 15 to 60 minutes after infection. Phage from the final sample can be evaluated individually, e.g., by ELISA, DNA sequencing, restriction enzyme fingerprinting, and so forth. They can also be analyzed en masse, e.g., by ELISA or by reformatting (see, e.g., U.S. Ser. No. 10/383,902). Identified peptides can be produced synthetically and tested, e.g., for a biological activity or other property. Identified antibodies (e.g., Fab's) can be produced as complete antibodies from mammalian cells, e.g., antibodies including a functional Fc domain, and tested, e.g., for antibody dependent cellular toxicity and/or complement dependent cellular toxicity.

Transfer of Host Cells

Another exemplary method includes transferring the infected cells after infection. This embodiment differs from the first in that cells that have been infected by the phage that are bound to target in a first vessel are transferred to a second vessel before progeny phage are released from the infected cells. The burst of progeny are released in the second vessel. The second vessel can include a fresh supply of the target compound. The target compound can be present in the vessel before transfer of the infected cells, or can be added subsequently.

This method can be used to reduce metabolism of the target compound (e.g., proteolysis, denaturation, or other modification of the target compound) and to provide a supply of the target compound that is free from phage, debris, and other substances that may be remnants from a previous round. The method also enables control of the amount of target compound in each cycle and the use of different target compounds in successive cycles. For example, one could use a peptide as the target compound in one cycle and a cell that expresses a protein that contains the peptide in another cycle.

The method can include:
a. Contacting a plurality of diverse display phage to a target compound;
b. separating phage that bind to the target compound from unbound phage;
c. Infecting host cells with the bound phage in a first vessel;
d. Transferring the infected cells to a second vessel,
e. Producing replicate phage from the infected cells in the presence of the target compound in the second vessel ("phage production");
f. separating phage that bind the target compound from the unbound phage and infected cells;
g. Repeating c. to e. one or more times, e.g., one to six times;
h. Recovering the bound phage, e.g., for individual characterization.

To transfer infected cells from one vessel to another, the target compound can be attached to a matrix, e.g., to Sepharose beads. A medium containing the cells is added to the matrix and incubated, e.g., for 10 to 20 or 10 to 15 minutes. Then the medium is separated from the matrix and added to the second vessel. For example, the matrix can be placed in a column and washed to remove the cells. In a related example, the target compound is attached to magnetic particles. A medium containing cells is added to the particles and incubated. A magnet is then used to remove the magnetic particles. A fresh supply of target-bound magnetic particles can be added to the vessel or the cells can be transferred to a second vessel. In still another example, the target compound is attached to the surface of a vessel. A medium containing cells is added to the vessel and incubated. Then magnetic particles that have an attached ligand (e.g., an antibody that binds to an outer membrane protein of *E. coli*, such as OmpA, OmpT, or LamB) that binds to the cells are added to the vessels. The cells are transferred to a new vessel using a magnet.

It is also possible to use target beads that have been blocked for varying times during successive cycles. The target beads include the target compound on an accessible surface. For example, the beads used in the first cycle can be blocked for one hour, whereas beads used in the second cycle can be blocked for two hours; beads used in the third cycle for three hours, and so on. Increased blocking time may increase the number of high affinity binding phage depending on the concentration of target compound bound to the beads and the temperature (Zhuang et al. 2001 *J. Biosci and Bioeng* 91:474-481.)

Washing times and conditions can also be varied from cycle to cycle. In one example, both blocking and washing times are decreased with successive cycles to increase the number of binders obtained from the selection process.

Cell-Surface Targets

The target compound can also be presented on the surface of a cell, e.g., a eukaryotic cell. This approach is particularly useful for selections and subsequent screenings to find ligands that bind to a membrane associated protein. Many target proteins are membrane-bound and are difficult to produce in native form (e.g., including glycosylation and other post-translational modifications such as proteolytic processing and accompanying conformational changes), except on cells.

One method for selecting members of a display library that bind to a target compound on the surface of a cell can include:
a. Contacting a plurality of diverse display phage to cells that present the target compound on their cell surface;
b. Separating phage that bind to the target-presenting cells from unbound phage;
c. Infecting host cells with the bound phage (e.g., by contacting the host cells to the target-presenting cells);
d. Separating the target-presenting cells from the host cells;
e. Producing replicate phage from the infected host cells;
f. Contacting the replicate phage to target-presenting cells (e.g., a new sample of such cells)
g. Separating phage that bind to the target-presenting cells from unbound phage
h. Repeating c. to g. one or more times, e.g., one to six times;
i. Recovering the bound phage, e.g., for individual characterization.

The target-presenting cells can be living or fixed. When live target-presenting cells are used, the plurality of diverse phage can be added to a medium that supports the target-presenting cells, e.g., to tissue culture medium. In some cases, agents that alter the metabolism or the behavior of target-presenting cells can also be used. For example, an agent that reduces the rate of endocytosis can be added to reduce internalization of the display phage.

The eukaryotic target-presenting cells can be separated from the host cells by a variety of methods. One exemplary method is differential sedimentation. For example, a brief (and/or low speed) centrifugation can be used to sediment the target-presenting cells while leaving the host cells in solution. (See, e.g., Belshe and Mufson. (1991). Textbook of Human Virology. Mosby Year Book, St. Louis, pp. 388). Another separation method relies on differential adherence. Eukaryotic cells can be adhered to a surface, e.g., a surface that includes a coating of extracellular matrix protein (e.g., fibronectin).

Generally target-presenting cells and host cells can also be separated by distinctive cell surface markers. For example, the target-presenting cells can be biotinylated and captured on streptavidin (Sv) beads. After contact with the diverse phage, the target-presenting cells on the beads are washed to remove non-binding phage. In another example, an antibody that binds to a cell-surface marker other than the target is used to attach the target-presenting cells to an insoluble support, e.g., beads.

Still other methods for separating the target-presenting cells from host cells include:

The host cells (e.g., *E. coli*) can be labeled with biotin and captured on Sv beads.

The host cells (e.g., *E. coli*) can include an accessible surface tag, e.g., a peptide sequence that binds a known partner. The peptide sequence can be a component (e.g., a heterologous component) of an outer surface protein. For example, a peptide having the amino acid sequence of "HPQ" (Devlin et al. 1990 *Science* 249(4967) pp. 404-406.) can be positioned in an outer loop of OmpA, LamB, or OmpT cell surface protein. Peptides having the amino acid sequence of "HPQF" (SEQ ID NO:1) frequently bind to Sv. Koebnik (*J. Bact.* (1999) 181(12)3688-3694) shows a schematic of the structure of *Escherichia coli* OmpA. Residues that are exposed on *E. coli* outer membrane comprise:

$$L1 = H_{19}DTGFINNNGPTHE_{32}, \quad \text{(SEQ ID NO: 2)}$$

$$L2 = P_{62}YKGSVENGAYK_{73}, \quad \text{(SEQ ID NO: 3)}$$

$$L3 = D_{105}TKSNVYGKNHDTG_{118}, \quad \text{(SEQ ID NO: 4)}$$
and $$L4 = I_{147}GDAHYIGTRPD_{158}. \quad \text{(SEQ ID NO: 5)}$$

Koebnik also reports that OmpA folds and assembles into the outer membrane when each of the loops is drastically shortened. Thus, the sequence and conformation of these loops are not essential to the transport, folding, or assembly of OmpA into the outer membrane of *E. coli*. The base sequence of *E. coli* OmpA is disclosed in GenBank entry: LOCUS ECOMPA, Accession V00307 J01654, Version V00307.1 GI:42159.

The amino-acid sequence WHPQFSS (SEQ ID NO:6) has been reported to bind Sv (Cwirla et al. (1990) *Proc Natl Acad Sci USA*, 87:6378-6382.). Cwirla et al. reported several other Sv-binding sequences and any of these could be used. The subsequence HPQ is the most important part of the motif. Thus one could, for example, replace the DNA encoding L1 with DNA that encodes the sequence L1A=$H_{19}$DTG $W_{23}$HPQFSS$_{29}$ THE$_{32}$ (SEQ ID NO:7) using strains and vectors similar to those reported by Koebnik. Note that the novel amino acids are shown bold. It is not essential to include all of WHPQFSS (SEQ ID NO:6); the loop

L1B=$H_{19}$DTGF HPQF GPTH$E_{32}$ (SEQ ID NO:8)

is likely to make cells that express this variant of OmpA bind Sv.

Alternatively, L2 could be replace with

L2A=$P_{62}$YKG$S_{66}$ $W_{67}$H$P_{69}$$Q_{69a}$$F_{69b}$$S_{69c}$$S_{69d}$ $G_{70}$AY$K_{73}$ (SEQ ID NO:9)

in which the loop has been lengthened. Note that residues 62-66 and 70-73 have not been altered and the Sv-binding sequence is bounded by flexible sequence (GS and GA). In and alternative example, L3 could be replaced by L3A=$D_{105}$TK$S_{108}$ $W_{109}$HPQFS$S_{114a}$ $H_{115}$DT$G_{118}$, (SEQ ID NO:10)

in which the loop is lengthened by one residue. A further example would be to replace L4 with L4A=$I_{147}$GD$A_{150}$ $W_{151}$HP$Q_{154}$$F_{154a}$$S_{154b}$ $T_{155}$RP$D_{158}$ (SEQ ID NO:11) in which residues 151-154 have been replaced with six residues including the HPQ motif.

Sousa et al. (*J. Bact.* (1998) 180(9)2280-2284.) disclose that large insertions can be made into *E. coli* LamB at position 153. For example, one could insert DNA encoding the amino-acid sequence GPCHPQFPRCYI (SEQ ID NO:12) at codon 153. Other binding sequences and epitopes can be used in addition to the examples provided here. Preferably such sequences can be specifically recognized and placed in an accessible position on the cell surface.

The host cells (e.g., *E. coli*) can be captured with an antibody that binds to the host cells (*E. coli*).

The target-presenting cells can be biotinylated.

The target-presenting cells can present a marker in addition to the target compound. The target-presenting cells can be captured using a binding partner (e.g. an antibody) that recognizes the marker. In one example, the marker is a peptide, such as HPQF (SEQ ID NO:1), that binds a known protein, such as Sv.

The target-presenting cells can be captured with beads known to bind adherent cells (e.g., "Microcarrier Beads" from Amersham-Pharmacia).

Phage that bind to the surface of the cell in the vicinity of a specific cell surface marker can be tagged (e.g., biotinylated) and then captured, e.g., using Sv. See, e.g., Osbourn et al. (1998) *Immunotechnology* 3:293.

In some implementations, the target-binding phage are separated from the target-presenting cells, e.g., prior to infection of the host cells. In one example, acid or base is used to dissociate the target-binding phage from the target-bearing cells. In another example in which the phage include a specific protease cleavage site between the displayed protein and the bacteriophage particle, the complex of target cells and bound phage can be treated with a protease that specifically cleaves the site. Cleavage releases the phage from the cells and enables recovery of the nucleic acids that encode proteins that bind to the target.

Specificity

The methods can also be used to identify proteins that bind to a particular part of the target compound (i.e. an epitope of interest) or that bind selectively, e.g., relative to a related non-target compound (such as a protein homolog). Criteria for selection may also include a particular minimum affinity, or affinity range.

The following example provides a method for isolating a protein that binds to an epitope that is defined by a given ligand.

a. Contacting a plurality of diverse display phage to a target compound;
b. Separating phage that bind to the target compound from unbound phage;
c. Providing the given ligand;
d. Separating phage that dissociate from the target compound in the presence of the given ligand;
e. Infecting host cells with the dissociated phage;
f. Producing replicate phage from the infected cells, e.g., in the presence of the target compound ("phage production");
g. Separating phage that bind the target compound from the unbound phage and the infected cells;
h. Repeating c. to g. one or more times, e.g., one to six times;
i. Recovering the bound phage or, again, phage dissociated by the given ligand. Recovered phage can be individually characterized.

The given ligand can be added in excess of its IQ for the target so that any phage that bind the epitope recognized by the given ligand are likely to be prevented from re-binding to the epitope after the given ligand is added. For example, a peptide that has $K_d$=40 nM might be added at a concentration of 5 μM. By competing and preventing rebinding of phage to the epitope, phage that display proteins that bind the epitope are maintained in the supernatant. The supernatant is removed from the immobilized target and added to growing $F^+$ *E. coli*. The supernatant also includes the given ligand as it is present in excess during the competition reaction. Phage in the supernatant infect the *E. coli* and more *E. coli* are produced.

To remove the given ligand from the medium so that replicates of the infecting phage are produced in a medium without the given ligand, the infected *E. coli* cells are sedimented and then resuspended in fresh growth medium. The target compound can be included or added to the fresh growth medium. The process can then be repeated two to five more times.

In other embodiments, it is also possible to include a competing compound, e.g., during phage production. The competing compound can be a compound that differs from the target compound, but is structurally similar to the target compound. In one embodiment, a model the structure of the competing compound can be superimposed on a model of the structure of the target compound with a root-mean-squared standard deviation of less than 2.5, 2, 1.5, or 1 Angstroms. In another embodiment, the target compound is a protein, and the competing compound is a related protein, e.g., a protein with at least 25, 35, 50, 60, 70, 80, 90, 95, or 99% identity to the target compound. The comparison of sequences and determination of percent identity between two sequences can be accomplished using a mathematical algorithm. In particular, the percent identity between two amino acid sequences is determined using the Needleman and Wunsch ((1970) *J. Mol. Biol.* 48:444-453) algorithm which has been incorporated into the GAP program in the GCG software package, using a Blossum 62 scoring matrix with a gap penalty of 12, a gap extend penalty of 4, and a frameshift gap penalty of 5. In still another embodiment, the target compound differs from the competing compound by less than 5, 4, 3, or 2 amino acids.

Phagemids

In some implementations, the diverse phage include phagemid particles. These implementations can include the addition of helper phage or other methods that supply bacteriophage genes necessary for producing replicate particles. An exemplary method includes:
  a. Contacting a plurality of diverse display phagemids to a target compound;
  b. Separating phagemids that bind to the target compound from unbound phagemids;
  c. Infecting host cells with the bound phagemids;
  d. Adding helper phage;
  e. Producing replicate phagemids from the infected cells in the presence of the target compound ("phagemid production");
  f. Separating phagemids that bind the target compound from the unbound phagemid, helper phage, and infected cells;
  g. Repeating c. to e. one or more times, e.g., one to six times;
  h. Recovering the bound phagemids, e.g., for individual characterization.

Immobilization

In many methods, the target compound becomes fixed to an immobilized support, e.g., before or after addition of the diverse phage.

Non-covalent attachment. A target compound can be attached to an insoluble support by a non-covalent interaction. This interaction can occur either before, during or after the target compound is contacted to a display library.

The target compound can be attached to one member of a binding pair. The insoluble support includes the other member of the binding pair. When the target compound and the insoluble support are mixed, the complementary binding pairs interact and attach the target compound to the support. The binding interaction between biotin and Sv is an exemplary high affinity non-covalent binding interaction. Other exemplary non-covalent interactions that can be used for binding pairs include: glutathione-S-transferase and glutathione (see, e.g., U.S. Pat. No. 5,654,176), hexa-histidine and $Ni^{2+}$ (see, e.g., German Patent No. DE 19507 166), and an antibody and a peptide epitope (see, e.g., Kolodziej and Young (1991) *Methods Enz.* 194:508-519 for general methods of providing an epitope tag).

Covalent Attachment. A target compound can also be covalently attached to an insoluble support. For example, the insoluble support might include a chemically reactive group, e.g., a thiol reactive, amine-reactive, or carboxylate-reactive group. The reactive group can be used to attach to a functional group on the target compound. For example, a thiol-reactive reagent such as iodoacetamide can be used to bond to a free cysteine on a target compound. Another exemplary reagent is NHS-sepharose affinity chromatography resin.

The target compound can be immobilized to any insoluble support, e.g., a matrix, bead, resin, planar surface, or immunotube. The insoluble support can be treated, e.g., coated with a blocking agent to prevent non-specific binding to the support. The target compound can be in solution (i.e., not immobilized) while phage are being produced. For example, the target compound can be biotinylated and contacted to immobilized Sv, e.g., after binding to phage in solution. In another example, the target compound is a chimeric protein, e.g., a GST-fusion protein. As a chimeric protein, the target compound can also be immobilized to an appropriate insoluble support after solution phase binding to phage.

In one embodiment, the display library is depleted of members that interact with the insoluble support in the absence of the target compound prior to selecting members of the library that bind the target using a support that includes the target compound. For example, the display library can be passed over Sv coated beads to remove members that bind to Sv. Then the library can be contacted to Sv coated beads that are bound by a biotinylated target compound to select library members that interact with the target compound.

It is also possible to add additional target compound during the phage production (step (d)). For example, if the target compound is bound to beads, additional target beads can be added. The addition of target compound can counter possible loss of functional target compound during exposure to the host cells.

Selection Methods

In one embodiment, magnetically responsive particles (e.g., paramagnetic beads) are used to capture display library members. The particles can include a capture reagent, e.g., which binds to the target compound or the target compound can be directly attached to the particle. In one example, Sv coated magnetic particles are used. The target compound is covalently linked to a biotin moiety. The target compound can be attached (before or after binding a display library member) to the magnetic particle. Magnetic particle separation can be automated, e.g., using a magnetic particle processor such as the KingFisher™ system of Thermo LabSystems, e.g., as described below.

In another embodiment, the display library is panned against the surface of a vessel, e.g., the bottom of a well of a microtitre plate. The method can be automated by a liquid handling device that can be used to add, remove, and transfer liquid to and from the vessel.

In still another embodiment, the display library is contacted to the target compound in a flow chamber, e.g., a chromatography column. Liquid can be flowed through the chamber at appropriate times, e.g., to separate binders from non-binders, and to deliver and/or remove host cells, etc. The flow chamber can also be closed, e.g., to prevent flow and allow for agitation of the chamber.

Automation

Various devices can used to automate the methods described herein. These devices include multi-well plate conveyance systems, magnetic bead particle processors, liquid handling units, colony picking units, and other robotics. These devices can be built on custom specifications or purchased from commercial sources, such as Autogen (Framingham Mass.), Beckman Coulter (USA), Biorobotics (Woburn Mass.), Genetix (New Milton, Hampshire UK), Hamilton (Reno Nev.), Hudson (Springfield N.J.), Labsystems (Helsinki, Finland), Packard Bioscience (Meriden Conn.), and Tecan (Mannedorf, Switzerland).

In some cases, the methods described herein include an automated process for handling magnetic particles. The target compound is immobilized on the magnetic particles. The KingFisher™ system, a magnetic particle processor from Thermo LabSystems (Helsinki, Finland), for example, can be used to select display library members against the target. The display library is contacted to the magnetic particles in a tube. The beads and library are mixed. Then a magnetic pin, covered by a disposable sheath, retrieves the magnetic particles and transfers them to another tube that includes a wash solution. The particles are mixed with the was solution. In this manner, the magnetic particle processor can be used to serially transfer the magnetic particles to multiple tubes to wash non-specifically or weakly bound library members from the particles. After washing, the particles can be transferred to a vessel that includes a medium that supports display library member amplification. In the case of phage display the vessel may also include host cells.

In some cases, e.g., for phage display, the processor can also separate infected host cells from the previously-used particles. The processor can also add a new supply of magnetic particles for an additional round of selection.

The use of automation to perform the selection can increase the reproducibility of the selection process as well as the through-put.

An exemplary magnetically responsive particle is the Dynabead® available from Dynal Biotech (Oslo, Norway). Dynabeads® provide a spherical surface of uniform size, e.g., 2 µm, 4.5 µm, and 5.0 µm diameter. The beads include gamma $Fe_2O_3$ and $Fe_3O_4$ as magnetic material. The particles are superparamagnetic as they have magnetic properties in a magnetic field, but lack residual magnetism outside the field. The particles are available with a variety of surfaces, e.g., hydrophilic with a carboxylated surface and hydrophobic with a tosyl-activated surface. Particles can also be blocked with a blocking agent, such as BSA or casein to reduce non-specific binding and coupling of compounds other than the target to the particle.

The target is attached to the paramagnetic particle directly or indirectly. A variety of target molecules can be purchased in a form linked to paramagnetic particles. In one example, a target is chemically coupled to a particle that includes a reactive group, e.g., a crosslinker (e.g., N-hydroxy-succinimidyl ester) or a thiol.

In another example, the target is linked to the particle using a member of a specific binding pair. For example, the target can be coupled to biotin. The target is then bound to paramagnetic particles that are coated with Sv (e.g., M-270 and M-280 Streptavidin Dynaparticles® available from Dynal Biotech, Oslo, Norway). In one embodiment, the target is contacted to the sample prior to attachment of the target to the paramagnetic particles.

In some implementations, automation is also used to analyze display library members identified in the selection process. From the final sample, individual clones of each display member can be obtained. Each member can be individually analyzed, e.g., to assess a functional property. Exemplary functional properties include: a kinetic parameter (e.g., for binding to the target compound), an equilibrium parameter (e.g., avidity, affinity, and so forth, e.g., for binding to the target compound), a structural or biochemical property (e.g., thermal stability, oligomerization state, solubility and so forth), and a physiological property (e.g., renal clearance, toxicity, target tissue specificity, and so forth) and so forth. Methods for analyzing binding parameters include ELISA, homogenous binding assays, and SPR. For example, ELISAs on a displayed protein can be performed directly, e.g., in the context of the phage or other display vehicle, or the displayed protein removed from the context of the phage or other display vehicle.

Each member can also be sequenced, e.g., to determine the nucleic acid sequence of the encoded protein that is displayed.

Additional exemplary methods of automating a library screens and selections are described in U.S. 2003-0129659.

Target Compounds

Generally, any molecular species can be used as a target compound. The target compound can be of a small molecule (e.g., a small organic or inorganic molecule), a protein, a nucleic acid, cells, and so forth. By way of example, a number of examples and configurations are described for targets. Of course, target compounds other than, or having properties other, than those listed below can also be used.

One class of target compounds includes polypeptides. Examples of such target compounds include small peptides (e.g., about 3 to 30 amino acids in length), single polypeptide chains, and multimeric polypeptides (e.g., protein complexes).

A protein target can be modified, e.g., glycosylated, phosphorylated, ubiquitinated, methylated, cleaved, disulfide bonded and so forth. Preferably, the polypeptide has a specific conformation, e.g., a native state or a non-native state. In one embodiment, the polypeptide has more than one specific conformation. For example, prions can adopt more than one conformation. Either the native or the diseased conformation can be a desirable target, e.g., to isolate agents that stabilize the native conformation or that identify or target the diseased conformation. In some cases, however, the target compound is unstructured, e.g., adopts a random coil conformation or lacks a single stable conformation. Agents that bind to an unstructured protein can be used to identify the protein when it is denatured, e.g., in a denaturing SDS-PAGE gel, or to separate unstructured isoforms of the protein for correctly folded isoforms, e.g., in a preparative purification process.

A few exemplary protein targets include: cell surface proteins (e.g., glycosylated surface proteins or hypoglycosylated variants), cancer-associated proteins, cytokines, chemokines, peptide hormones, neurotransmitters, cell surface receptors (e.g., cell surface receptor kinases, seven transmembrane receptors, virus receptors and co-receptors, extracellular matrix binding proteins, or a cell surface protein (e.g., of a mammalian cancer cell or a pathogen). In some embodiments, the polypeptide is associated with a disease, e.g., cancer.

Target compounds that are proteins and that can be produced by a bacterial source can be produced by the host cells that support phage replication. For example, the host cells can be transformed with a recombinant nucleic acid that encodes the target compound. Expression of the recombinant nucleic acid results in secretion of the target compound into the periplasm and extracellular milieu where it can bind to replicates of the display phage. Such target compounds can then be immobilized, e.g., by a ligand (such as an antibody) that binds to a region of the target compound for which binding proteins are not being sought or by a member of a binding pair which binds to a corresponding member that is attached to the target compound. For example, the target compound can be produced as a fusion protein to a tag (e.g., a 6HIS or GST fusion protein). After secretion, the target compound can be immobilized to an insoluble matrix that includes a binding member that binds to the tag. Examples of such tags and binding members include: glutathione-S-transferase, and glutathione; chitin binding protein and chitin; Cellulase (CBD) and cellulose; maltose binding protein and amylose, or maltose; dihydrofolate reductases and methotrexate; FKBP and FK506.

Types of Display Libraries

May aspects of the method described here can be applied to any type of display library. Exemplary display libraries include phage display, cell display, ribosome display, and mRNA-protein fusions.

Phage Display. One format utilizes viruses, particularly bacteriophages. This format is termed "phage display." The protein component is typically covalently linked to a bacteriophage coat protein. The linkage results form translation of a nucleic acid encoding the protein component fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for Ff filamentous phage (phage f1, fd, and M13) as well as other bacteriophage (e.g. T7 bacteriophage and lambdoid phages; see, e.g., Santini (1998) *J. Mol. Biol.* 282:125-135; Rosenberg et al. (1996) *Innovations* 6:1-6; Houshm et. al. (1999) *Anal Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In a preferred embodiment, the fusion is to a domain of the gene III protein, e.g., the anchor domain or "stump," (see, e.g., U.S. Pat. No. 5,658,727 for a description of the gene III protein anchor domain). It is also possible to physically associate the protein being displayed to the coat using a non-peptide linkage, e.g., a non-covalent bond or a non-peptide covalent bond. For example, a disulfide bond and/or c-fos and c-jun coiled-coils can be used for physically association (see, e.g., Crameri et al. (1993) *Gene* 137:69 and WO 01/05950).

The valency of the protein component can also be controlled. Cloning of the sequence encoding the protein component into the complete phage genome results in multivariant display since all replicates of the gene III protein are fused to the protein component. For reduced valency, a phagemid system can be utilized. In this system, the nucleic acid encoding the protein component fused to gene III is provided on a plasmid, typically of length less than 7000 nucleotides. The plasmid includes a phage origin of replication so that the plasmid is incorporated into bacteriophage particles when bacterial cells bearing the plasmid are infected with helper phage, e.g. M13K07. The helper phage provides an intact copy of gene III and other phage genes required for phage replication and assembly. The helper phage has a defective origin such that the helper phage genome is not efficiently incorporated into phage particles relative to the plasmid that has a wild type origin.

Bacteriophage displaying the protein component can be grown and harvested using standard phage preparatory methods, e.g. PEG precipitation from growth media.

After selection of individual display phages, the nucleic acid encoding the selected protein components, by infecting cells using the selected phages. Individual colonies or plaques can be picked, the nucleic acid isolated and sequenced.

Cell-Based Display. In still another format the library is a cell-display library. Proteins are displayed on the surface of a cell, e.g., a eukaryotic or prokaryotic cell. Exemplary prokaryotic cells include *E. coli* cells, *B. subtilis* cells, spores (see, e.g., Lu et al. (1995) *Biotechnology* 13:366). Exemplary eukaryotic cells include yeast (e.g., *Saccharomyces cerevisiae, Schizosaccharomyces pombe, Hanseula*, or *Pichia pastoris*). Yeast surface display is described, e.g., in Boder and Wittrup (1997) *Nat. Biotechnol.* 15:553-557.

In one embodiment, variegated nucleic acid sequences are cloned into a vector for yeast display. The cloning joins the variegated sequence with a domain (or complete) yeast cell surface protein, e.g., Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1). The vector can be configured to express two polypeptide chains on the cell surface such that one of the chains is linked to the yeast cell surface protein. For example, the two chains can be immunoglobulin chains.

In one embodiment, yeast display cells are amplified in the presence of a target compound. For example, a library of display cells can be contacted to a target compound. Cells that bind can be separated from ones that do not, e.g., under conditions that do not support cell division. After separation, the binding cells can be amplified, e.g., by providing conditions that do support cell division. After or during amplification, an insoluble support that includes the target compound can be washed to remove cells that do not bind or that do not bind stringently.

In one example, the condition that is altered is temperature. For example, binding may be at 4° C., whereas amplification may be 30° C. In another example, the yeast display cells may include a temperature sensitive mutation, e.g., a mutation that prevents cell division at high temperature such as CDC28, CDC37, or CDC14. Cells can be maintained at the restrictive temperature during binding and then at the permissive temperature for amplification.

Ribosome Display. RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999)*J Immunol Methods.* 231(1-2):119-35. The in vitro translation process can be effected in the presence of the target compound. RNA amplification, e.g., using Qβ polymerase, can also be effected in the presence of the target compound.

Protein-Nucleic Acid Fusions. Another format utilizes protein-nucleic acid fusions. Protein-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and crosslinked to the protein.

Again, the in vitro translation process can be effected in the presence of the target compound. Nucleic acid amplification, particularly amplification methods at 42° or less (e.g., an isothermal amplification method, such as rolling circle amplification), can also be effected in the presence of the target compound.

A variety of proteins can be displayed by a display library. The methods described herein are applicable to a library that displays any type of protein, including libraries that display linear and cyclic peptides, small proteins, large proteins, and antibodies. The libraries can be constructed by diversifying a protein scaffold, by derivation from cDNA or genomic nucleic acid, or by providing a diverse set of synthetic sequences (e.g., random peptides).

Scaffolds. Exemplary scaffolds for display can include: antibodies (e.g., Fab fragments, single chain Fv molecules (scFv), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, CMTI (*Cucurbida maxima* trypsin inhibitor) and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). Another useful type of scaffolding domain is the immunoglobulin (Ig) domain. Methods using immunoglobulin domains for display are also known (see, e.g., Haard et al. (1999) *J. Biol. Chem* 274:18218-30; Hoogenboom et al. (1998) *Immunotechnology* 4:1-20. and Hoogenboom et al. (2000) *Immunol Today* 21:371-8).

Artificial Peptides. The binding ligand can include an artificial peptide, e.g., an artificial peptide of 30 amino acids or less. The artificial peptide can include one or more disulfide bonds. Other artificial peptides, so-called "linear peptides," are devoid of cysteines. artificial peptides may have little or no structure in solution (e.g., unstructured), heterogeneous structures (e.g., alternative conformations or "loosely structured), or a singular native structure (e.g., cooperatively folded). Some artificial peptides adopt a particular structure when bound to a target molecule. Some exemplary artificial peptides are so-called "cyclic peptides" that have at least disulfide bond, and, for example, a loop of about 4 to 12 non-cysteine residues.

Peptide sequences that bind a molecular target are selected from a phage-display library. After identification, such peptides can be produced synthetically or by recombinant means. The sequences can be incorporated (e.g., inserted, appended, or attached) into longer sequences.

Flow Chamber

In one embodiment, a flow chamber is used to amplify a display library member. For example, the flow chamber includes an inlet for flowing in a medium for cell growth and wash solutions, and an outlet for disposal of the medium and for collecting samples of interest, e.g., from a elution. The flow chamber may also include an aperture into which a magnetic field inducer can be inserted into the flow chamber in order to capture magnetically responsive particles in a zone surrounding the sheath. The flow chamber can further include a stirrer, e.g., which is rotated in order to circulate the growth medium and wash solutions through the chamber. When the magnetic field inducer is removed, the stirrer can be used to agitate the magnetically responsive particles. The flow chamber can also include an oxygenation system, a temperature controller, and glucose, pH and $CO_2$ monitors.

The flow chamber can be used to select members of a cell-display library. For example, a yeast cell display library that displays immunoglobulin molecules is mixed in the flow chamber with magnetically responsive particles that include a target compound. The magnetic field inducer is inserted into the sheath to capture the particles. PBS (phosphate buffered-saline) or another wash solution is flushed through the chamber. Flow is arrested, and the magnetic field is released to agitate the particles. Then the magnetic field is reapplied. This wash method can be repeated for a number of cycles.

After washing, media, e.g., YEPD or minimal media, can be flowed through the chamber under conditions that allow the cells to grow and multiply. After an interval sufficient for a desired number of cell divisions elapses, the wash method can be repeated, e.g., with a more stringent wash solution.

The system can include repeatedly washing and growing of the cells as required. The use of the flow chamber for cell growth and multiplication allows for immediate amplification of cells that bind to the magnetically responsive particles and can obviate the need for some of the external manipulations that are required for multiple selection cycles. As a result the cells are amplified in the presence of the target which is attached to the magnetically responsive particles. Similarly other replicable entities can be grown in the flow chamber (or any flow chamber herein) so that the replicable entities can be amplified in the presence of a target compound. For example, phage display library members can be amplified by addition of host cells (and helper phage for phagemids) for sufficient time that a burst is formed.

Fractions of the solutions (e.g., media or wash solutions) that are emerging from the flow chamber can be collected. In particular, fractions can be taken during any wash step, and during the most stringent washing step, i.e., an elution step. The fraction can be plated, e.g., onto agar plates with yeast media, in order to form colonies from the individual cells that are present in the fraction. The fraction can also be diluted into liquid media to amplify the cells outside of the growth chamber.

In another embodiment, the flow chamber has a single port, e.g., a flask with an upper opening that is sealable.

Fluid is removed and provided from the single port. In still other embodiments, the flow chamber has multiple ports, e.g., three or more ports.

Example 1

Approximately 100 µl of Dynal Sv coated magnetic beads (Dynal M280) were blocked with 500 µl of 2% milk in PBS (MPBS) for 30 minutes. Following a wash step to remove the excess milk, $3 \cdot 10^{11}$ Fab-displaying phage from a Fab-fragment phage display library diluted in MPBS was incubated with the blocked Sv beads in a total volume of 500 µl for 1 hour at room temperature. The Sv magnetic beads were collected and the unbound phage were removed by aspiration. The beads were washed three times in 1×PBS followed by the addition of 500 µl of XL1Blue-MRF' cells (Stratagene) at an $OD_{600}$ of 0.50 in 2×YT. The mixture was incubated at 37° C. for 15 minutes at which time 5 µl of 100 mM IPTG was added to achieve a final concentration of 1 mM IPTG. At 20 minutes, the bacteria were transferred to a 30° C. air shaker for an additional 25 minutes for a total incubation time of 45 minutes. The bacteria were removed and the beads were washed three times with 500 µl of 0.01% Tween-20 PBS. An additional 500 µl of XL1Blue-MRF' cells were supplemented to the beads and the process of incubating and washing was repeated for a total of 3 rounds. The 500 µl of phage infected bacteria from each round were titered on ampicillin-containing plates as well as grown overnight in 10 mL of 2×YT containing 1 mM IPTG at 30° C. The resulting phage were purified by standard PEG precipitation.

Three parallel experiments were carried out. In the first, the temperature was held at 37° C. for 20 minutes and then dropped to 30° C. for 25 minutes. In the second, the temperature of incubation was held constant at 37° C. for 45 minutes. In the third, the temperature was held constant at 30° C.

The titres of the various rounds are shown in Table 1. In the headings, "37×20+30×25" denotes the experiment in which the first 20 minutes of incubation was at 37° C. and the final 25 minutes was at 30° C., "37×45" denotes the experiment in which 37° C. was used for 45 minutes, and "30×45" denotes the experiment in which 30° C. was used for 45 minutes.

TABLE 1

|  | 37 × 20 + 30 × 25 | 37 × 45 | 30 × 45 |
| --- | --- | --- | --- |
| cfu round 1/foi | 5.8e7/1.95E-4 | 8e7/2.7E-4 | 5.1e7/1.7E-4 |
| cfu round 2/foi | 5.1e5/0.009 | 1.2e6/0.015 | 7.5e5/0.012 |
| cfu round 3/foi | 7.3e4/0.14 | 5.4e4/0.045 | 4.8e4/0.063 |

Example 2

A target protein that includes a nickel chelating tag was contacted to a phage display library that displays Fabs. The mixture was then bound to nickel magnetic beads. After washing the beads three times, XL1 Blue MRF' cells were contacted to the beads. Phage produced by these cells were allowed to bind to the target protein on the beads. The XL1 Blue MRF' cells were removed. The phage-target-bead complexes were washed to remove unbound phage. For a second round of amplification, fresh XL1 Blue MRF' cells were contacted to the beads. This was repeated one more time, thus providing a total of three rounds of amplification.

The output FAb-displaying phage from both rounds two and three from either of the selection campaigns were screened by ELISA to determine whether the isolated phage bound to the target protein. The target protein was passively immobilized on Immulon 2 HB 96-well ELISA plates (Thermo Labsystems) overnight at 4° C. The plates were blocked for thirty minutes with phosphate buffered saline containing 3% (w/v) bovine serum albumin (BSA) and 0.05% (v/v) Tween-20. Overnight bacterial growths of FAb-displaying phage were then incubated with the target protein for 1 hour at room temperature. FAb-displaying phage were detected with an anti-M13 HRP-conjugated antibody. In this particular example, the hit rate for both rounds 2 and 3 was about 69%.

Example 3

The following is an example of a method of amplifying a display library of phagemids in the presence of a target compound. The method includes the following steps:
1) Mix phagemid library with biotinylated target
2) Capture target and binding phage on Sv beads
3) Wash away non-binding phagemid (cold target can be used for a limited time to elute weak binders; as many washes as needed can be performed)
4) Add F+ cells and growth medium
5) Incubate for time T1 (between 30 min to 120 minutes, optionally with antibiotic which could be added after time T2 to select for infected cells)
6) Aliquot cells into empty vials (one per target) and plate as round 1
7) Set round counter R=1
8) Into each vial, add helper phage and target on Sv beads (if necessary additional target could be added after the helper phage, burst of phagemid is expected ~30-45 minutes after addition of helper phage)
9) At time T3, wash away cells and non-binding phage (optionally can use cold target-wash for a limited time to elute weak binders)
10) Add cells and GM
11) Incubate for time T4 (e.g., 30 min to 120 minutes; probably=T1) (antibiotic can be added after time T5 (probably=T2) to select for infected cells)
12) Make round counter R=R+1
13) Transfer an aliquot of cells to new counter
14) Plate an aliquot of cells for colonies as round "R" (2, 3, . . . )
15) Go back to step 8 as needed.
Other embodiments are within the following claims.

What is claimed:

1. A method of selecting phage that encode a target binding protein from a plurality of phage particles, the method comprising:
   a) contacting a plurality of diverse phage particles with a first target to form phage-target complexes, wherein each phage of the plurality displays a heterologous protein component on its surface and each phage includes a nucleic acid encoding the heterologous protein component, and wherein each phage-target complex comprises a phage from the plurality, the heterologous protein displayed on which binds the first target;
   b) separating the phage-target complexes from unbound phage particles;
   c) contacting host cells with the separated phage-target complexes in a suitable growth medium so that the host cells are infected by the phage particles of the phage-target complexes to yield a first population of infected cells;
   d) incubating the first population of infected cells in the presence of a second target under conditions allowing for replication of the phage particles, thereby forming phage-target complexes that include replicate phage particles that bind to the second target;
   e) separating replicate phage particles that do not bind to the second target from the replicate phage-target complexes; and
   f) contacting host cells with the replicate phage target complexes so that host cells are infected with the replicate phage particles of the complexes to yield a second population of infected cells, wherein the second population of infected cells produce phage particles that encode heterologous proteins binding to both the first target and the second target;

wherein the first target and the second target are different.

2. The method of claim 1, wherein the first target is immobilized to a support prior to step (a).

3. The method of claim 1, wherein the first target is immobilized to a support during step (a).

4. The method of claim 1, wherein the second target is immobilized to a support prior to step (d).

5. The method of claim 1, wherein the second target is immobilized during step (d).

* * * * *